United States Patent
Isaacson et al.

(10) Patent No.: US 12,251,527 B2
(45) Date of Patent: Mar. 18, 2025

(54) CATHETER HAVING A CLOSED TIP AND SLIT FOR A PERIPHERAL INTRAVENOUS CATHETER ASSEMBLY

(71) Applicant: Becton, Dickinson and Company, Franklin Lakes, NJ (US)

(72) Inventors: S. Ray Isaacson, Layton, UT (US); Bart D. Peterson, Farmington, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 428 days.

(21) Appl. No.: 16/573,731

(22) Filed: Sep. 17, 2019

(65) Prior Publication Data

US 2020/0094023 A1   Mar. 26, 2020

Related U.S. Application Data

(60) Provisional application No. 62/734,006, filed on Sep. 20, 2018.

(51) Int. Cl.
*A61M 25/06* (2006.01)
*A61M 25/00* (2006.01)
(Continued)

(52) U.S. Cl.
CPC .... *A61M 25/0606* (2013.01); *A61M 25/0097* (2013.01); *A61M 25/0625* (2013.01);
(Continued)

(58) Field of Classification Search
CPC .......... A61M 25/0097; A61M 25/0625; A61M 2025/0048; A61M 2039/064; A61M 2039/1083; A61M 2039/1088; A61M 25/007; A61M 39/22; A61M 2039/2426; A61M 25/0102; A61M 2025/0076
See application file for complete search history.

(56) References Cited

U.S. PATENT DOCUMENTS 4,327,722 A * 5/1982 Groshong ............. A61M 5/158
604/510
4,338,942 A * 7/1982 Fogarty ............... A61M 25/104
604/101.02
(Continued)

FOREIGN PATENT DOCUMENTS

CN   102355923 A   2/2012
CN   103124578 A   5/2013
(Continued)

*Primary Examiner* — Chelsea E Stinson
*Assistant Examiner* — Hamza A Darb
(74) *Attorney, Agent, or Firm* — Kirton McConkie; Whitney Blair; Kevin Stinger

(57) ABSTRACT

An apparatus may include a connector, which may include a proximal end and a distal end. The distal end of the connector may include a male luer adapter, which may be configured to couple with a proximal end of a catheter adapter. The apparatus may include a catheter, which may include a proximal end secured within the connector. The catheter may be configured to extend through an indwelling peripheral intravenous catheter. The catheter may include a closed distal end and a slit adjacent to the closed distal end. The slit may be closed under normal physiological pressures.

12 Claims, 8 Drawing Sheets

(51) Int. Cl.
*A61M 25/01* (2006.01)
*A61M 39/10* (2006.01)
*A61M 39/06* (2006.01)

(52) U.S. Cl.
CPC ............... *A61M 2025/0048* (2013.01); *A61M 2039/064* (2013.01); *A61M 2039/1083* (2013.01); *A61M 2039/1088* (2013.01)

(56) References Cited

U.S. PATENT DOCUMENTS

| | | | |
|---|---|---|---|
| 4,671,796 A * | 6/1987 | Groshong | A61M 25/00 604/170.01 |
| 4,701,166 A | 10/1987 | Groshong et al. | |
| 4,871,356 A | 10/1989 | Haindl et al. | |
| 4,988,356 A | 1/1991 | Crittenden et al. | |
| 5,215,527 A * | 6/1993 | Beck | A61M 25/007 604/164.09 |
| 6,356,791 B1 * | 3/2002 | Westlund | A61N 1/057 607/125 |
| 8,066,670 B2 | 11/2011 | Cluff et al. | |
| 2002/0156430 A1 | 10/2002 | Haarala et al. | |
| 2004/0176743 A1 | 9/2004 | Morris et al. | |
| 2008/0294145 A1 * | 11/2008 | Eddings | A61M 25/0097 604/533 |
| 2009/0275919 A1 * | 11/2009 | Todd | A61M 25/0102 604/509 |
| 2010/0036329 A1 * | 2/2010 | Razack | A61M 39/0613 604/256 |
| 2012/0095404 A1 * | 4/2012 | Massengale | A61B 8/481 604/528 |
| 2018/0289932 A1 | 10/2018 | Isaacson et al. | |

FOREIGN PATENT DOCUMENTS

| | | |
|---|---|---|
| CN | 203539776 U | 4/2014 |
| EP | 0162982 A2 | 12/1985 |
| EP | 0250891 | 1/1988 |
| EP | 0351864 | 1/1990 |
| EP | 2289590 | 3/2011 |
| GB | 2472407 A | 2/2011 |
| JP | 2002336360 A | 11/2002 |
| JP | 2007175297 A | 7/2007 |
| JP | 2008188324 A | 8/2008 |
| WO | 2009/135174 | 11/2009 |
| WO | 2013108482 A1 | 7/2013 |

* cited by examiner

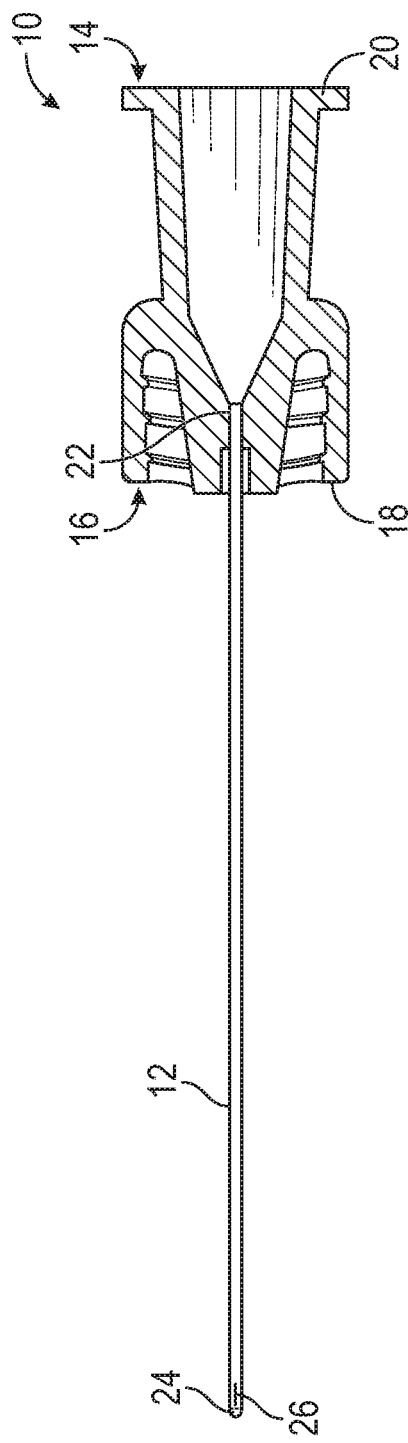
FIG. 1A
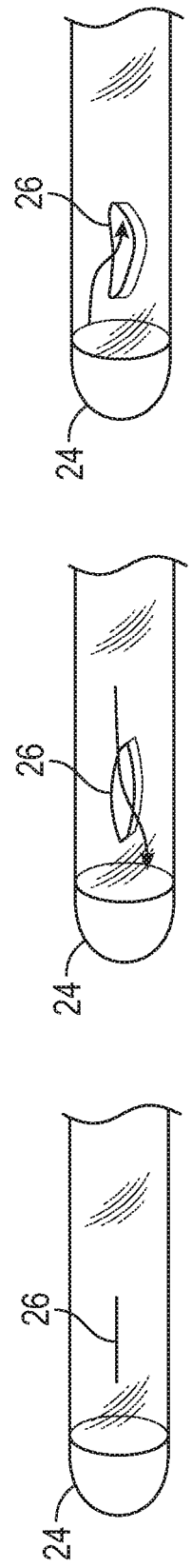
FIG. 1B
FIG. 1C
FIG. 1D

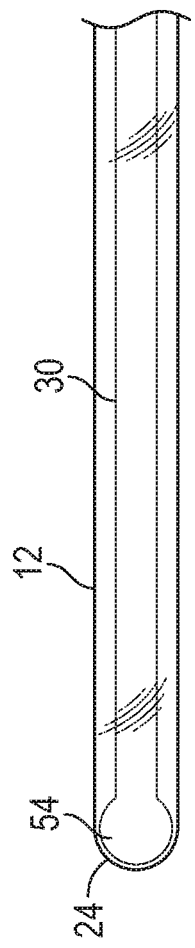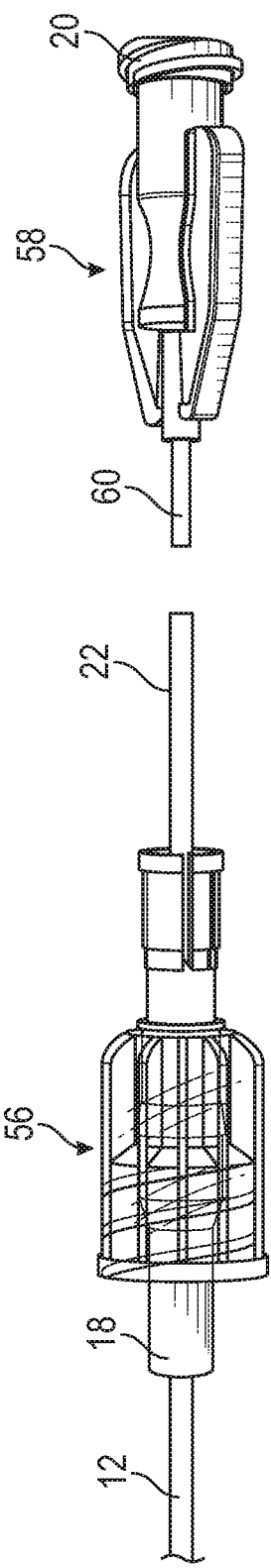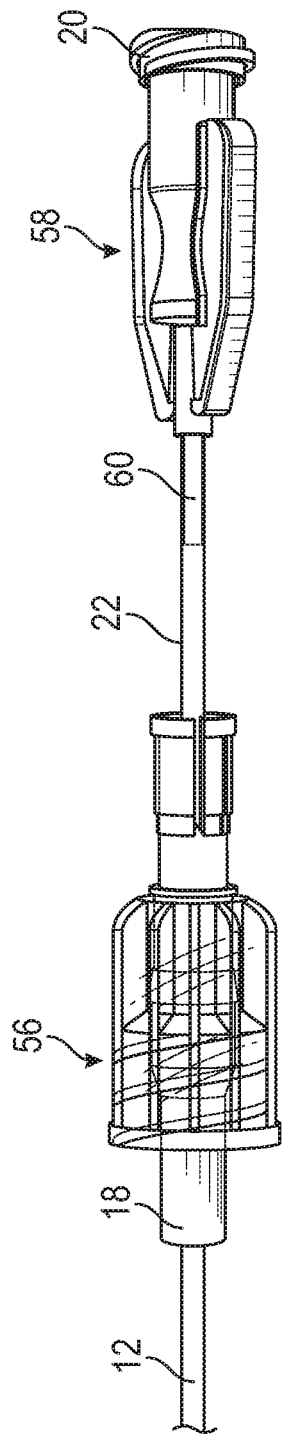
FIG. 3D
FIG. 4A
FIG. 4B

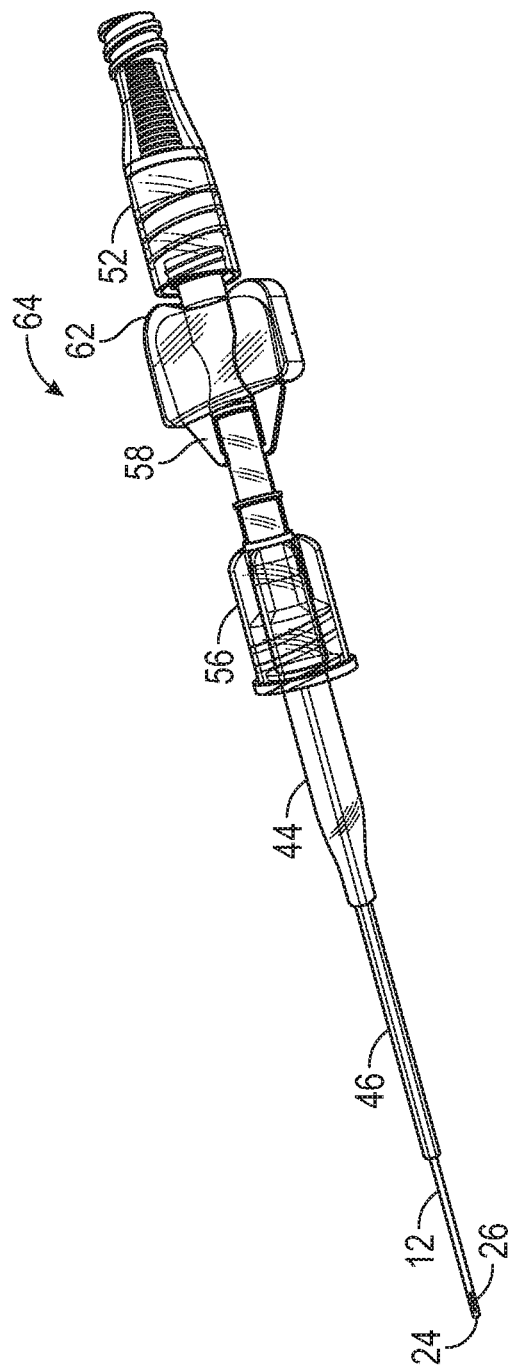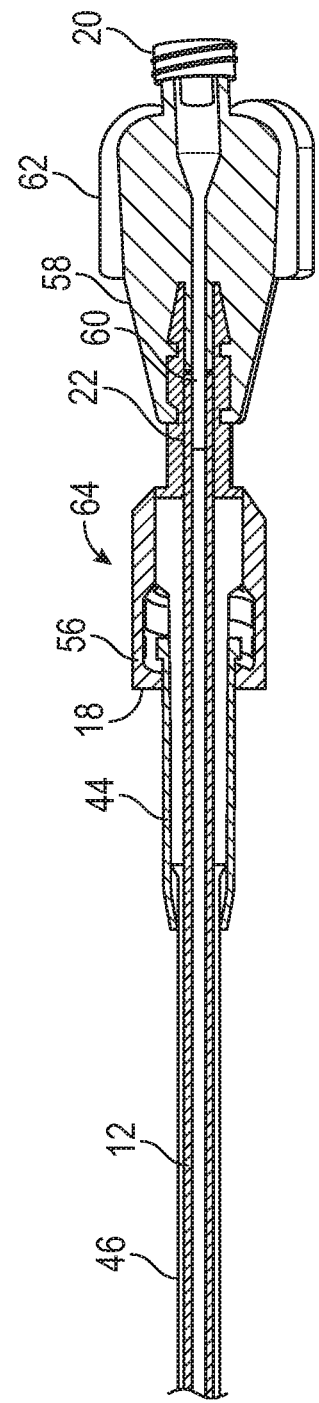
FIG. 5B
FIG. 5C

400 →

INSERT A FIRST CATHETER THROUGH A SECOND CATHETER OF AN INDWELLING PERIPHERAL INTRAVENOUS CATHETER ASSEMBLY AND INTO VASCULATURE OF A PATIENT, WHEREIN A PROXIMAL END OF THE FIRST CATHETER IS SECURED WITHIN A CONNECTOR, THE FIRST CATHETER HAVING A CLOSED DISTAL END AND A SLIT ADJACENT THE CLOSED DISTAL END, WHEREIN THE SLIT IS CLOSED UNDER NORMAL PHYSIOLOGICAL PRESSURES 402

COUPLE THE CONNECTOR TO THE INDWELLING PERIPHERAL INTRAVENOUS CATHETER ASSEMBLY, WHEREIN THE FIRST CATHETER EXTENDS BEYOND A DISTAL END OF THE SECOND CATHETER WHEN THE CONNECTOR IS COUPLED TO THE INDWELLING PERIPHERAL INTRAVENOUS CATHETER ASSEMBLY 404

FIG. 6

CATHETER HAVING A CLOSED TIP AND SLIT FOR A PERIPHERAL INTRAVENOUS CATHETER ASSEMBLY

RELATED APPLICATIONS

This application claims the benefit of U.S. Provisional Application No. 62/734,006, filed Sep. 20, 2018, and entitled "CATHETER HAVING A CLOSED TIP AND SLIT FOR A PERIPHERAL INTRAVENOUS CATHETER ASSEMBLY", which is incorporated herein in its entirety.

BACKGROUND

Infusion therapy, a common healthcare procedure, may be facilitated by a vascular access device. Hospitalized, home care, and other patients receive fluids, pharmaceuticals, and blood products via a vascular access device inserted into the vascular system. Blood withdrawal is another common healthcare procedure that may be facilitated by a vascular access device.

A vascular access device may access a peripheral or central vasculature of a patient. A vascular access device may be indwelling for short term (days), moderate term (weeks), or long term (months to years). A vascular access device may be used for continuous infusion therapy or for intermittent therapy.

A common type vascular access device is an over-the-needle peripheral intravenous catheter (PIVC). As its name implies, the "over-the-needle" PIVC may be mounted over an introducer needle having a sharp distal tip. The sharp distal tip may be used to pierce skin and the vasculature of the patient. Insertion of the PIVC into the vasculature may follow the piercing of the vasculature by the introducer needle. The introducer needle and the PIVC are generally inserted at a shallow angle through the skin into the vasculature of the patient with a bevel of the introducer needle facing away from the skin of the patient. Once placement of the introducer needle within the vasculature has been confirmed, the clinician may temporarily occlude flow in the vasculature and withdraw the introducer needle, leaving the PIVC in place for future fluid infusion and/or blood withdrawal.

Currently, there may be several limitations to the use of a PIVC for fluid infusion or blood draw. The PIVC or vein may narrow, collapse, or clog with time, leading to failure of the PIVC. In some instances, risk of occlusion of the PIVC may lead to increased flushing and risk of infection. PIVCs may also be prone to removal from the vein, which may lead to infiltration or extravasation.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to devices, systems, and methods for fluid transfer through a placed or indwelling peripheral intravenous catheter ("PIVC") assembly. In some instances, the PIVC may be fairly easily placed within the vein of the patient by means of an introducer needle, which may pierce skin and vasculature of a patient to facilitate placement of the PIVC within the vein. In some embodiments, the devices, systems, and methods of the present disclosure may take advantage of the introducer needle for placement of the PIVC, while providing benefits of a second catheter with a closed distal end and a valve to reduce occlusion, flushing, and risk of infection. In some embodiments, the second catheter with the closed distal end and valve may be threaded through the PIVC into the vein of the patient.

In the prior art, PIVCs may be prone to clotting because blood is allowed to diffuse into the PIVC. In some embodiments described in the present disclosure, the valve of the second catheter may include a slit. In some embodiments, the slit may open under positive or negative pressure to allow fluid infusion or blood withdrawal. In some embodiments, the second catheter may be resistant to occlusion and thrombosis because the slit may be closed and blood may not be allowed to diffuse into the second catheter under normal physiological pressures. Thus, in some embodiments, the PIVC assembly that includes the second catheter may be flushed less frequently, such as, for example, once per week, instead of, for example, once per shift of a clinician.

In some embodiments, the second catheter and the valve may reduce flushing of the PIVC assembly from a high number of flushes, such as, for example, 3 times per day and 7 days per week (for a total of 21 flushes per week) to a low number of flushes, such as, for example, one flush per week. Reducing flushing may not only decrease a risk of infection, but may also free the clinician to focus on other matters in a healthcare setting.

One drawback of the PIVC of the prior art is that it may be easy to pull out of the vein due to several factors, including its length or extension into the vein. When the PIVC pulls out of the vein, this may lead to infiltration and/or extravasation. In some embodiments, the devices, systems, and methods of the present disclosure may reduce or eliminate infiltration and extravasations. In further detail, in some embodiments, even if a distal tip of the PIVC pulls out of the vein, the second catheter may be longer than the PIVC and positioned further down the vein, preventing removal of the second catheter from the vein and subsequent infiltration and extravasation.

In some embodiments, the second catheter may not be long enough to reach the heart, which may allow the second catheter to be placed within the vein without ultrasound and/or fluoroscopy in a simple placement procedure involving only a few steps.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 1A is a cross-sectional view of an example connector and example catheter having a closed distal end and slit, according to some embodiments;

FIG. 1B is an upper perspective view of the slit of FIG. 1A is a closed position, according to some embodiments;

FIG. 1C is an upper perspective view of the slit of FIG. 1A in an open position during fluid infusion, according to some embodiments;

FIG. 1D is an upper perspective view of the slit of FIG. 1A in an open position during blood withdrawal, according to some embodiments;

FIG. 3D is a cross-sectional view of an example ball feature, according to some embodiments;

FIG. 4A is an upper perspective view of another example connector that includes a first piece and a second piece in a step of an example assembly process, according to some embodiments;

FIG. 4B is an upper perspective view of the connector of FIG. 4A during another step of the assembly process, according to some embodiments;

FIG. 5B is an upper perspective view of the connector of FIG. 5A having an example push tab, according to some embodiments;

FIG. 5C is a cross-sectional view of the connector of FIG. 5A, according to some embodiments; and FIG. 6 is a flow chart illustrating an example method, according to some embodiments.

DESCRIPTION OF EMBODIMENTS

Figure 2:
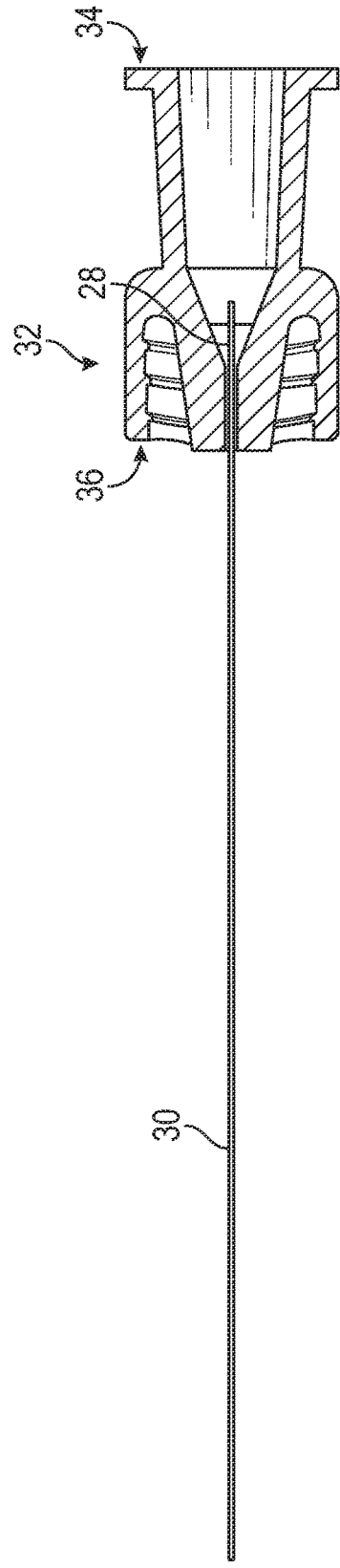
FIG. 2 is a cross-sectional view of an example guidewire hub and example guidewire, according to some embodiments.

The present disclosure relates generally to devices, systems, and methods for fluid transfer through a placed or indwelling peripheral intravenous catheter ("PIVC") assembly. In some instances, the PIVC may be fairly easily placed within the vein of the patient by means of an introducer needle, which may pierce skin and vasculature of a patient to facilitate placement of the PIVC within the vein. In some embodiments, the devices, systems, and methods of the present disclosure may take advantage of the introducer needle for placement of the PIVC, while providing benefits of a second catheter with a closed distal end and a valve to reduce occlusion, flushing, and risk of infection. In some embodiments, the second catheter with the closed distal end and valve may be placed within the PIVC and extend through the PIVC into a vein of a patient.

Referring now to FIG. 1A, an example connector 10 and example second catheter 12 are illustrated, according to some embodiments. In some embodiments, the connector 10 may include a proximal end 14 and a distal end 16. In some embodiments, the distal end 16 of the connector 10 may include a luer adapter, such as a slip or thread male or female luer adapter, which may be configured to couple with a proximal end of a catheter adapter of an indwelling PIVC assembly to provide a fluid tight seal. In some embodiments, the distal end 16 of the connector 10 may include a male luer adapter having a freely rotating collar, which may allow coupling of the connector 10 to a catheter adapter without having to rotate the catheter 12. FIG. 1A illustrates the distal end 16 of the connector 10 having an example male luer adapter 18, according to some embodiments.

In some embodiments, the proximal end 14 of the connector 10 may include another luer adapter, such as a slip or thread male or female luer adapter, which may be coupled to a blood collection device, a fluid infusion device, or a needleless connector, for example. FIG. 1A illustrates the proximal end 14 of the connector 10 having an example female luer adapter 20, according to some embodiments.

In some embodiments, a proximal end 22 of the second catheter 12 may be secured within the connector 10. In some embodiments, the second catheter 12 may extend from the distal end 16 of the connector 10. In some embodiments, the second catheter 12 may include a closed distal end 24 and a valve adjacent the closed distal end 24. In some embodiments, the valve may include a slit 26. In some embodiments, under normal physiological pressures, the slit 26 may be closed, as illustrated in FIG. 1A. In some embodiments, the closed distal end 24 may be rounded or bullet-shaped.

In some embodiments, all or a portion of the second catheter 12 may be constructed of silicon. In some embodiments, a portion of the second catheter 12 that includes the slit 26 may be constructed of silicon. In some embodiments, all or a portion of the second catheter 12 may be constructed of polyurethane or another suitable plastic. In some embodiments, the portion of the second catheter 12 that includes the slit 26 may be constructed of polyurethane or another suitable plastic.

The second catheter 12 may have an outer diameter less than an inner diameter of a 16 g or 18 g PIVC. In some embodiments, the outer diameter of the second catheter 12 may be less than about 0.052-0.054 inches. In some embodiments, the outer diameter of the second catheter 12 may be less than about 0.036-0.039 inches. In some embodiments, the outer diameter of the second catheter 12 may be between about 0.034-0.036 inches. In some embodiments, the second catheter 12 may include lubrication in order to thread the second catheter 12 through the indwelling PIVC assembly. In some embodiments, the second catheter 12 may snugly fit within the PIVC.

In some embodiments, dimensions of the second catheter 12 may vary. In some embodiments, the second catheter 12 may be about 3 inches in length. In some embodiments, the second catheter 12 may be less than about 5 inches in length. In some embodiments, the second catheter 12 may have a length between about 2 and 5 inches.

Referring now to FIG. 1B, the slit 26 is illustrated in a closed position, according to some embodiments. In some embodiments, the slit 26 may include a longitudinal slit oriented along a longitudinal axis of the catheter 12. In some embodiments, when the slit 26 is in the closed position, opposing faces of the slit 26 may contact each other. In some embodiments, the slit 26 may be in the closed position and sealed under normal physiological pressures, preventing fluid from flowing through the slit 26. In some embodiments, the second catheter 12 may be resistant to occlusion and thrombosis because the slit 26 may be closed under normal physiological pressures, preventing blood from diffusing into the second catheter 12. Thus, in some embodiments, the PIVC assembly (illustrated, for example, in FIGS. 3B-3C) that includes the second catheter 12 may be flushed less frequently, such as, for example, once per week, instead of, for example, once per shift of a clinician.

In some embodiments, the second catheter 12 and the slit 26 may reduce flushing of the PIVC assembly from a high number of flushes, such as, for example, 3 times per day and 7 days per week (for a total of 21 flushes per week) to a low number of flushes, such as, for example, one flush per week. Reducing flushing may not only decrease a risk of infection, but may also free the clinician to focus on other matters in a healthcare setting.

Referring now to FIG. 1C-1D, in some embodiments, in response to a predetermined pressure differential, the slit 26 may open. In some embodiments, the slit 26 may open during infusion of fluid into the patient, as illustrated, for example, in FIG. 1C. In some embodiments, the slit 26 may open during withdrawal of blood from the patient, as illustrated, for example, in FIG. 1D.

Referring now to FIG. 2, in some embodiments, a proximal end 28 of a guidewire 30 may be secured within a guidewire hub 32 having a proximal end 34 and a distal end 36. In some embodiments, the guidewire 30 may extend from the distal end 36 of the guidewire hub 32. In some embodiments, the guidewire 30 may be constructed of metal or another suitable material to provide stiffening when disposed within the catheter 12.

In some embodiments, the proximal end 34 of the guidewire hub 32 may include a luer adapter, such as a slip or thread male or female luer adapter. In some embodiments, the proximal end 34 may include a female luer adapter, which may be used to pre-prime a system (illustrated, for example, in FIG. 3B) with saline. In some embodiments, the distal end 36 of the guidewire hub 32 may include a luer adapter, such as a slip or thread male or female luer adapter. FIG. 2 illustrates the distal end 36 of the guidewire hub 32 having a male luer adapter 38, which may be configured to couple with the proximal end 14 of the connector 10.

Figure 3A:
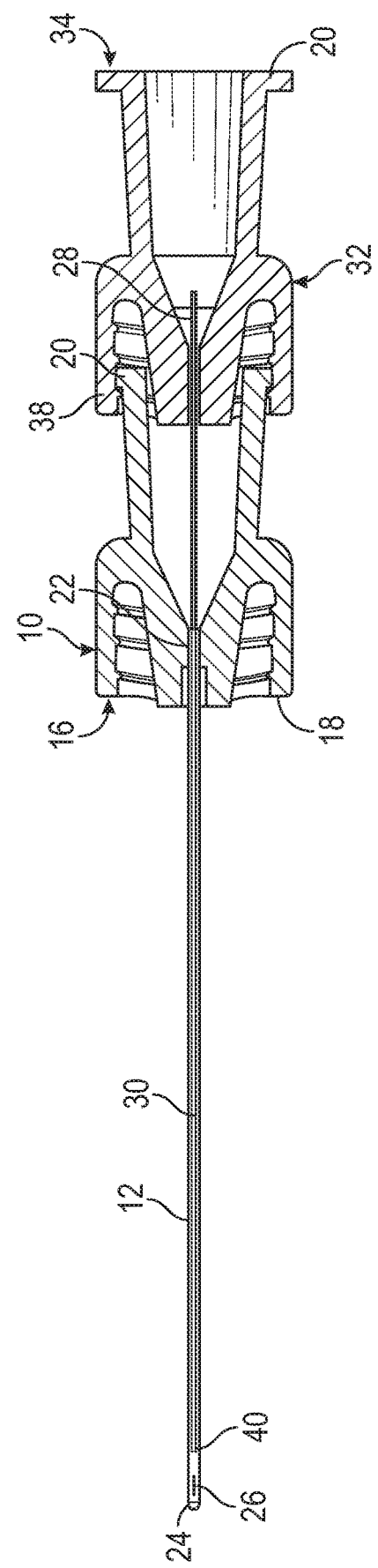
FIG. 3A is a cross-sectional view of the guidewire hub of FIG. 2 coupled with the connector of FIG. 1A.

Referring now to FIG. 3A, in some embodiments, the guidewire hub 32 may be removably coupled to the proximal end 14 of the connector 10. In some embodiments, the guidewire 30 may be disposed within the second catheter 12 in response to the guidewire hub 32 being coupled to the proximal end 14 of the connector 10. In some embodiments, the guidewire 30 may be stiff enough to push through any bends in the second catheter 12 and/or through vessel geometry, until the second catheter 12 is disposed in a position within the vein for fluid delivery and/or blood withdrawal. In some embodiments, the guidewire 30 may extend to the closed distal end 24 of the second catheter 12. In some embodiments, the distal end 40 of the guidewire 30 may extend near or adjacent the closed distal end 24 of the second catheter 12.

Figure 3B:
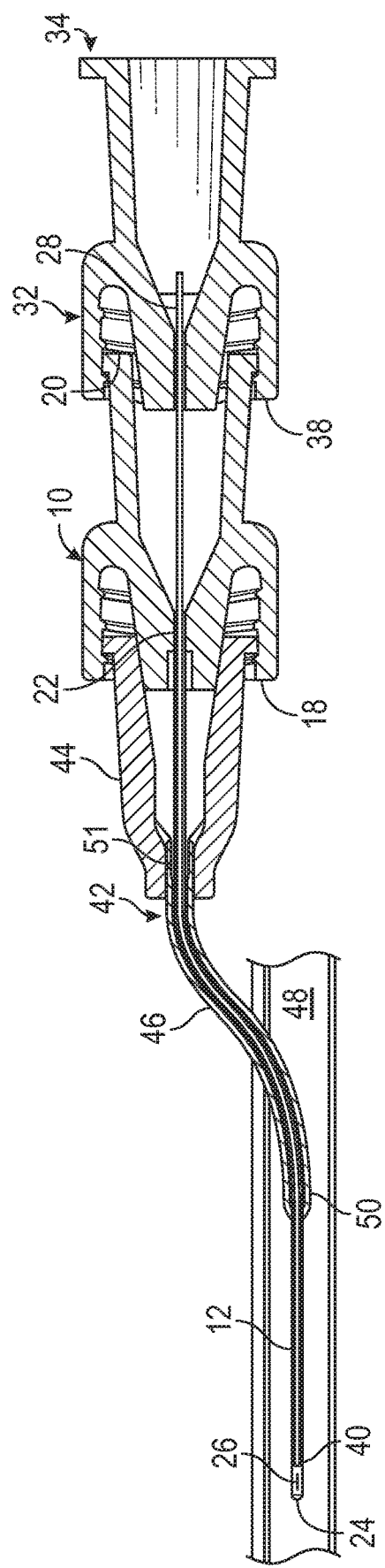
FIG. 3B is a cross-sectional view of the connector of FIG. 1A and the guidewire hub of FIG. 2 coupled with an example catheter assembly, according to some embodiments.

Referring now to FIG. 3B, an example indwelling PIVC assembly 42 is illustrated, according to some embodiments. In some embodiments, the PIVC assembly 42 may include a catheter adapter 44 and a PIVC 46 extending distally from the catheter adapter 44. In some embodiments, a proximal end 51 of the PIVC 46 may be secured within the catheter adapter 44. In some embodiments, the catheter adapter 44 may include a blood control feature such as a septum (not illustrated) or any number of other features known in the art.

In some embodiments, the PIVC 42 may be "over-the-needle." As its name implies, the "over-the-needle" PIVC 42 may be mounted over an introducer needle (not illustrated) having a sharp distal tip. The sharp distal tip may be used to pierce skin and the vein 48 of the patient. Insertion of the PIVC 42 into the vasculature may follow the piercing of the vein 48 by the introducer needle. The introducer needle and the PIVC 42 may be inserted at a shallow angle through the skin into the vein 48 of the patient. Once placement of the PIVC 42 within the vein 38 has been confirmed, the clinician may temporarily occlude flow in the vein 48 and withdraw the introducer needle, leaving the PIVC 42 in place for future fluid infusion and/or blood withdrawal. Non-limiting examples of a needle assembly are illustrated in U.S. patent application Ser. No. 15/481,166, filed Apr. 6, 2017, entitled "INTRAVENOUS CATHETER ASSEMBLY WITH SAFETY CLIP," which is hereby incorporated by reference in its entirety.

In some embodiments, the distal end 16 of the connector 10 may be removably coupled with a luer connector of the PIVC assembly 42, providing a seal. In some embodiments, the guidewire hub 32 and the connector 10 may be coupled together prior to coupling of the connector 10 to the proximal end 14 of the catheter adapter 44 and extension of the catheter 12 through the PIVC 46. In some embodiments, the guidewire hub 32 and the connector 10 may be coupled together during manufacturing and/or prior to packaging, such that the guidewire hub 32 and the connector 10 are already connected when a user removes them from packaging. In some embodiments, after the PIVC assembly 42 is inserted into the vein 48 and the introducer needle is removed, the connector 10, which may have the guidewire hub 32 previously coupled, may be coupled to the proximal end 14 of the catheter adapter 44, and the catheter 12 may extend through the PIVC 46. In some embodiments, the guidewire 30 disposed within the catheter 12 may aid movement of the catheter 12 through the PIVC assembly 42 and into the vein 48.

In some embodiments, when the connector 10 is coupled to the catheter adapter 44, the second catheter 12 may extend beyond a distal end 50 of the PIVC 46. In some embodiments, the second catheter 12 may extend about 1 inch beyond the distal end 50 of the PIVC 46. In some embodiments, the second catheter 12 may extend about 2 inches beyond the distal end 50 of the PIVC 46. In some embodiments, the second catheter 12 may extend between about 1 and 2 inches beyond the distal end 50 of the PIVC 46. In some embodiments, the second catheter 12 may extend between about 2 and 3 inches beyond the distal end 50 of the PIVC 46. In some embodiments, the second catheter 12 may extend less than about 1 inch beyond the distal end 50 of the PIVC 46. In some embodiments, the second catheter 12 may extend more than about 2 inches beyond the distal end 50 of the PIVC 46. In some embodiments, the second catheter 12 may not be long enough to reach the heart, which may allow the second catheter 12 to be placed within the vein 48 without ultrasound and/or fluoroscopy in a simple placement procedure involving only a few steps as described in the present disclosure. In some embodiments, the second catheter 12 may extend between about 3 and 5 inches from the connector 10. In some embodiments, the second catheter 12 may extend less than 5 inches from the connector 10. In some embodiments, the second catheter 12 may extend about 5 inches from the connector 10.

Figure 3C:
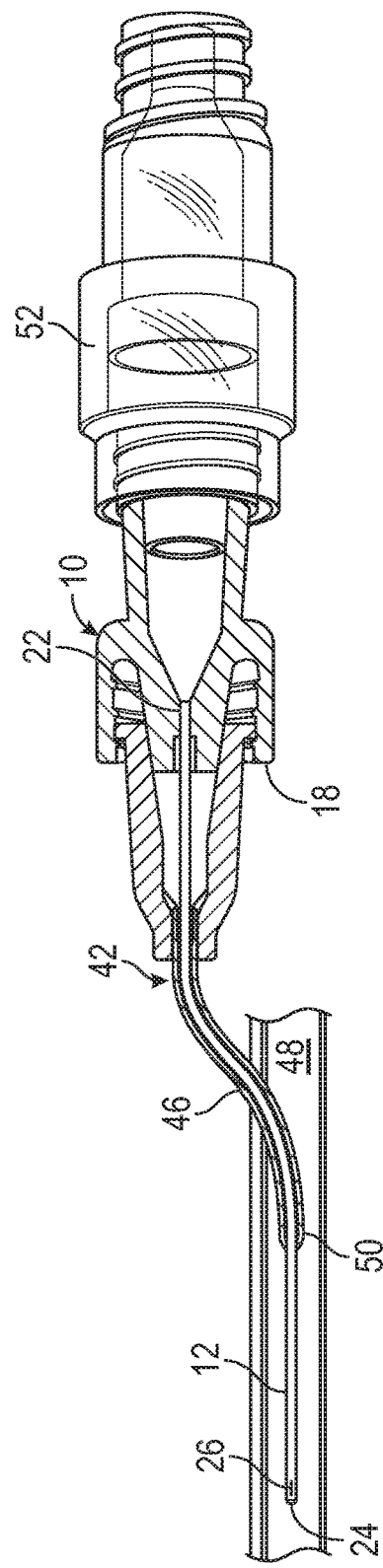
FIG. 3C is a cross-sectional view of the connector of FIG. 1A coupled with the catheter assembly of FIG. 3B and an example needleless connector, according to some embodiments.

Referring now to FIG. 3C, in some embodiments, after the guidewire 30 is used to place the catheter 12 within the PIVC assembly 42, the guidewire 30 may be removed by uncoupling the guidewire hub 32 from the connector 10. In some embodiments, after the guidewire hub 32 is removed from the proximal end 14 of the connector 10, a fluid infusion device and/or a blood withdrawal device may be coupled to the proximal end 14 of the connector 10 and fluid infusion and/or blood withdrawal may occur via the PIVC assembly 42 and the catheter 12. In some embodiments, the connector 10 may be uncoupled from the PIVC assembly 42 and the second catheter 12 removed from the PIVC 46 for high-pressure fluid infusion through the PIVC 46.

In some embodiments, a needleless connector 52 or another type of connector may be coupled to the proximal end 14 of the connector 10. In some embodiments, the needleless connector 52 may be coupled to the proximal end 14 of the connector 10 after the guidewire hub 32 is removed from the proximal end 14 of the connector 10. In some embodiments, after the guidewire hub 32 is removed from the proximal end 14 of the connector 10, a fluid infusion device and/or a blood withdrawal device may be coupled to the needless connector 52 and fluid infusion and/or blood withdrawal may occur via the PIVC assembly 42 and the catheter 12. In some embodiments, various types of needleless connectors 52 may be used. Some non-limiting examples of needleless connectors are described in U.S. Pat. No. 8,066,670, filed Nov. 5, 2007, entitled "VASCULAR ACCESS DEVICE SEPTUM VENTING," which is hereby incorporated by reference.

Referring now to FIG. 3D, in some embodiments, the distal end 40 of the guidewire 30 may include a rounded or ball feature 54. In some embodiments, the ball feature 54 may be smooth. In some embodiments, the closed distal end 24 of the second catheter 12 may allow the guidewire 30 to include the ball feature 54. In some embodiments, the ball feature 54 may contact the closed distal end 24 and facilitate pushing of the second catheter 12 into the vein 48. In some embodiments, the ball feature 54 may be disposed proximate the closed distal end 24 of the second catheter 12.

In some embodiments, the connector 10 may be monolithically formed as a single unit. In some embodiments, the connector 10 may be constructed of multiple pieces. Referring now to FIGS. 4A-4D, in some embodiments, another example connector 55 is illustrated, according to some embodiments. In some embodiments, the connector 55 may include or correspond to the connector 10 of FIGS. 1-3. In some embodiments, the connector 55 may include one or more features of the connector 10. In some embodiments, the connector 10 may include one or more features of the connector 55.

In some embodiments, the connector 55 may include a distal piece 56 and a proximal piece 58, which may be coupled together. In some embodiments, the distal piece 56 and the proximal piece 58 may be coupled together during manufacture and/or prior to packaging, such that the distal piece 56 and the proximal piece 58 are pre-assembled or already connected when the user removes them from packaging. In some embodiments, the distal piece 56 and the proximal piece 58 may be coupled via a snap fit, an interference fit, adhesive, welding, or another suitable method. In some embodiments, the distal piece 56 and the proximal piece 58 may be monolithically formed as a single unit.

In some embodiments, the proximal piece 58 may include a tubular element 60, which may be positioned within the proximal end 22 of the second catheter 12. In some embodiments, the tubular element 60 may include an outer diameter slightly less than an inner diameter of the second catheter 12 such that the tubular element 60 snugly fits within the proximal end 22 of the second catheter 12. In some embodiments, the tubular element 60 may be hollow, and the guidewire 30 may extend through the tubular element 60. In some embodiments, the tubular element 60 may be constructed of metal or another suitable material.

FIG. 4A illustrates the tubular element 60 being inserted into the second catheter 12, according to some embodiments. In some embodiments, a length of the second catheter 12 may be fixed or the length of the second catheter 12 may be manually modified by the user. In some embodiments, the connector 55 may facilitate manual modification of the length of the second catheter 12 at or just prior to a time of use. In further detail, in some embodiments, the user may trim the proximal end 22 of the catheter 12 such that the length of the second catheter 12 is a desired clinically relevant length. In some embodiments, the trimmed second catheter 12 can then be threaded onto the tubular element 60. In some embodiments, the distal piece 56 and the proximal piece 58 can then be coupled together to form a fluid tight seal.

FIG. 4B illustrates the tubular element 60 fully inserted into the second catheter 12, according to some embodiments. In FIGS. 4A-4B, the second catheter 12 extends through the distal piece 56, according to some embodiments. In some embodiments, the steps illustrated in FIGS. 4A-4B may be performed during manufacture and/or prior to packaging. In some embodiments, the distal end 16 of the connector 10 may include the male luer adapter 18. In some embodiments, the proximal end 14 of the connector 10 may include the female luer adapter 20, which may be coupled to a fluid infusion device, a blood withdrawal device, the needleless connector 52, or another device.

Figure 4C:
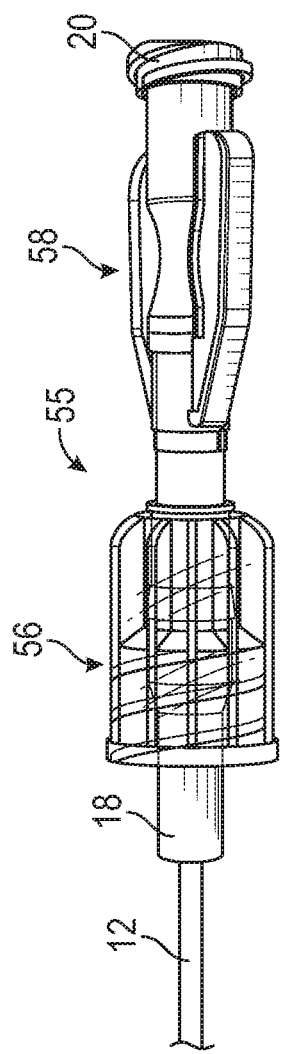
FIG. 4C is an upper perspective view of the connector of FIG. 4A fully assembled, according to some embodiments.
Figure 4D:
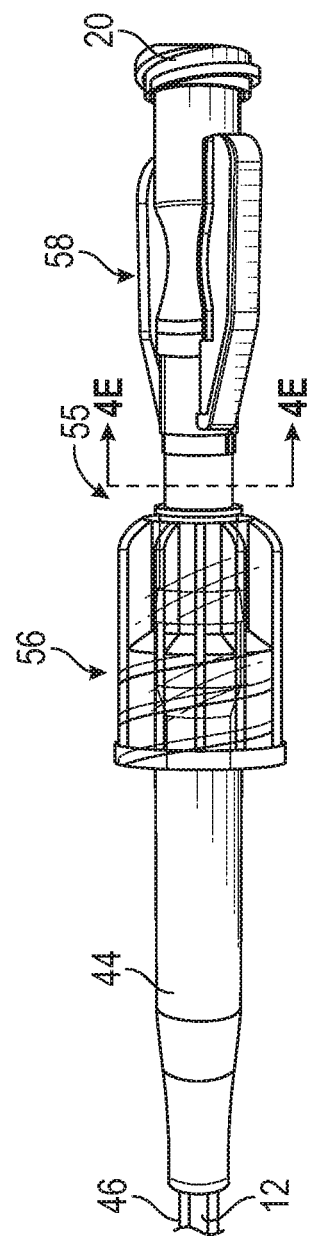
FIG. 4D is an upper perspective view of the connector of FIG. 4A coupled to an example catheter assembly, according to some embodiments.

Referring now to FIG. 4C, the distal piece 56 is illustrated coupled to the proximal piece 58, according to some embodiments. In some embodiments, the distal piece 56 and the proximal piece 58 may be coupled via an interference fit, as illustrated in FIG. 4C. Referring now to FIG. 4D, in some embodiments, the fully assembled connector 10 and the second catheter 12 may be coupled to a proximal end of the catheter adapter 44, similar to as illustrated in FIG. 3A, for example. In some embodiments, the guidewire hub 32 may be coupled to the proximal end 14 of the connector 10, and the guidewire 30 may extend into the second catheter 12.

In some embodiments, the distal piece 56 may include a compression element 63, which may include, for example, an annular sleeve. In some embodiments, the compression element 63 may be disposed in a lumen of the distal piece 56. In some embodiments, a length of the compression element 63 may be greater than, equal to, or less than a length of the tubular element 60. In some embodiments, the compression element 63 may keep the second catheter 12 on the tubular element 60 during infusion, under high pressure, and/or when the second catheter 12 swells. In some embodiments, the compression element 63 may put radial pressure on the proximal end 22 of the second catheter 12 at a location of the tubular element 60, which may facilitate securement of the tubular element 60 within the proximal end 22 and decrease a likelihood of the proximal end 22 coming off of the tubular element 60. In some embodiments, the compression element 63 may provide a backup fluid tight seal against high pressures.

Figure 4E:
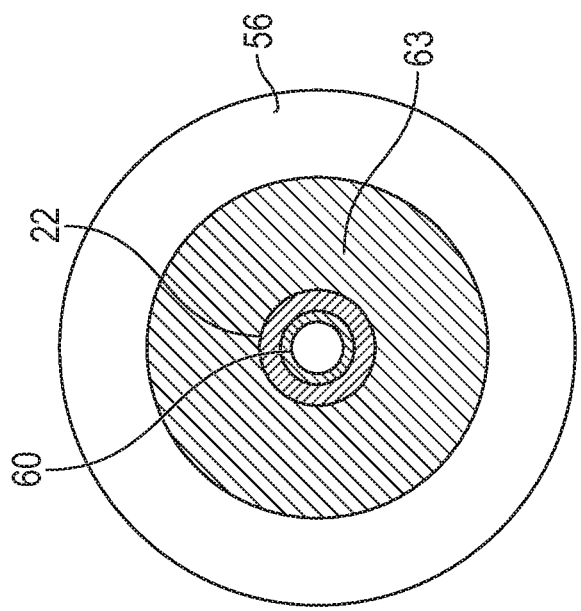
FIG. 4E is a cross-sectional view of the connector of FIG. 4A along the line 4E-4E of FIG. 4D, according to some embodiments.
Figure 5A:
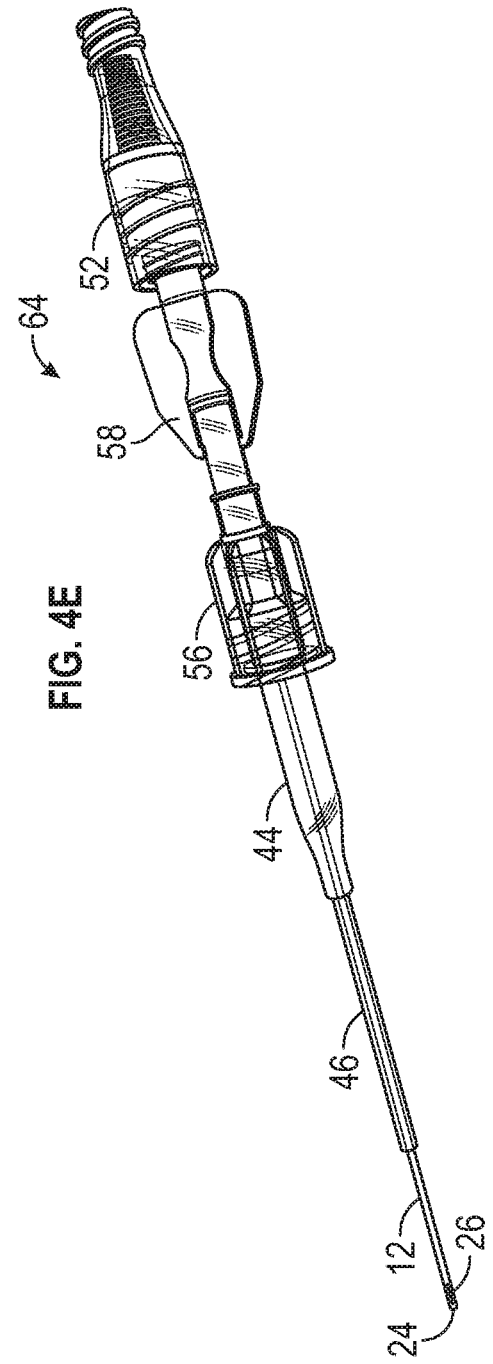
FIG. 5A is an upper perspective view of another example connector, according to some embodiments.

Referring now to FIG. 5A, another connector 64 is illustrated, according to some embodiments. In some embodiments, the connector 64 may include or correspond to the connector 10 of FIGS. 1-3 and/or the connector 55 of FIG. 4. In some embodiments, the connector 64 may include one or more features of the connector 10 and/or the connector 55. In some embodiments, the connector 10 and/or the connector 55 may include one or more features of the connector 64.

In some embodiments, the distal piece 56 of the connector 64 may be coupled to the catheter adapter 44. In some embodiments, the proximal piece 14 of the connector 64 may include a luer adapter, such as a slip or thread male or female luer adapter, which may be coupled to a blood collection device, a fluid infusion device, or a needleless connector, for example. FIG. 5C illustrates the proximal end 14 of the connector 64 having an example female luer adapter 20, according to some embodiments. In some embodiments, the needleless connector 52 may be coupled to the female luer adapter 20, as illustrated, for example, in FIGS. 5A-5B.

Referring now to FIG. 5B, in some embodiments, the connector 64 may include a grip 62, which may extend from a winged portion 61 of the proximal piece 58. Referring now to FIG. 5C, an example snap fit between the distal piece 56 and the proximal piece 58 is illustrated.

Referring now to FIG. 6, in some embodiments, a method 400 may begin at block 402. In block 402, a first catheter may be inserted or threaded through a second catheter of an indwelling PIVC assembly and into vasculature of a patient. In some embodiments, the first catheter may correspond to the second catheter 12 described with respect to one or more of FIGS. 1-5. In some embodiments, the second catheter and the PIVC assembly may correspond to the PIVC 46 and the PIVC assembly 42, respectively, described with respect to one or more of FIGS. 1-5. In some embodiments, a proximal end of the first catheter may be secured within a connector, such as the connector 10 of FIGS. 1-3, the connector 55 of FIG. 4, or the connector 64 of FIG. 5.

In some embodiments, the first catheter may include a closed distal end and slit adjacent the closed distal end. In some embodiments, the slit may be closed under normal physiological pressures. In some embodiments, block 402 may be followed by block 404.

At block 404, the connector may be coupled to the indwelling PIVC. In some embodiments, the first catheter may extend beyond a distal end of the second catheter when the connector is coupled to the indwelling PIVC assembly.

Although illustrated as discrete blocks, various blocks of method 400 may be divided into additional blocks, combined into fewer blocks, or eliminated, depending on the desired implementation. In some embodiments, the method 400 may include, when the connector is coupled to the indwelling PIVC assembly, uncoupling a guidewire hub from a proximal end of the connector and removing a guidewire from within the first catheter. In some embodiments, the guidewire hub and the guidewire may correspond to the guide wire hub 32 and the guidewire 30 described with respect to one or more FIGS. 1-5.

In some embodiments, the method 400 may include using the indwelling PIVC assembly coupled with the connector to infuse fluid or withdraw blood from a patient at a prolonged time after placement of the indwelling peripheral intravenous catheter assembly within vasculature of the patient. In some embodiments, the prolonged time may include more than about 4, 6, 8, 10, 12, 24, or 72 hours. In some embodiments, the prolonged time may include more than 1 week. In some embodiments, the prolonged time may include more than 1 month. In some embodiments, the first catheter may be inserted into the vasculature of the patient without use of fluoroscopy and ultrasound.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. An apparatus, comprising:
a connector having a distal piece and a proximal piece, wherein the distal piece and the proximal piece are coupled together in a snap fit or an interference fit, a distal end of the distal piece of the connector having a male luer adapter configured to couple with a proximal end of a catheter adapter, a proximal end of the proximal piece of the connector having a female luer adapter; and
a catheter secured within the distal piece of the connector, the catheter extending from the distal end of the distal piece of the connector, the catheter having a closed distal end and a slit adjacent the closed distal end, wherein the slit is closed under normal physiological pressures, wherein the proximal piece comprises a tubular element snugly inserted inside the proximal end of the catheter, the tubular element having an outer diameter slightly less than an inner diameter of the catheter;
a guidewire hub comprising a male luer adapter removably coupled to the female luer adapter of the proximal piece of the connector; and
a guidewire having a proximal end and a distal end, the guidewire extending from the distal end of the guidewire hub and disposed within the catheter, wherein the proximal end of the guidewire is secured within the guidewire hub.

2. The apparatus of claim 1, wherein the guidewire extends through the tubular element, wherein the tubular element is constructed of metal.

3. The apparatus of claim 1, wherein the catheter is constructed of silicon.

4. The apparatus of claim 1, wherein the catheter is constructed of polyurethane.

5. The apparatus of claim 1, wherein an outer diameter of the catheter is between 0.034 and 0.036 inches.

6. The apparatus of claim 1, further comprising a peripheral intravenous catheter assembly comprising the catheter adapter and a peripheral intravenous catheter extending distally from the catheter adapter, wherein the male luer adapter of the distal end of the distal piece of the connector is coupled with the proximal end of the catheter adapter, wherein the catheter extends beyond the distal end of the peripheral intravenous catheter.

7. The apparatus of claim 6, wherein the first catheter extends between about one and two inches beyond the distal end of the peripheral intravenous catheter.

8. The apparatus of claim 1, wherein a distal end of the guidewire comprises a spherical ball feature.

9. A method, comprising:
inserting into a vasculature of a patient a peripheral intravenous catheter assembly mounted over an introducer needle having a sharp distal tip such that the introducer needle extends through a peripheral intravenous catheter of the peripheral intravenous catheter assembly;
after inserting into the vasculature of the patient the peripheral intravenous catheter assembly mounted over the introducer needle, withdrawing the introducer needle from the peripheral intravenous catheter assembly and leaving the peripheral intravenous catheter assembly within the vasculature;
after withdrawing the introducer needle from the peripheral catheter assembly, flushing the peripheral intravenous catheter assembly with saline; and
after flushing the peripheral intravenous catheter assembly, pushing a second catheter coupled to a guidewire through the peripheral intravenous catheter of the peripheral intravenous catheter assembly and into vasculature of a patient, wherein the second catheter is secured within a connector, the second catheter having a closed distal end and a slit adjacent the closed distal end, wherein the slit is closed under normal physiological pressures, wherein the guidewire is disposed within the second catheter to facilitate the pushing of the second catheter through the peripheral intravenous catheter, wherein in response to pushing the second catheter coupled to the guidewire through the second peripheral intravenous catheter, the second catheter and the guidewire are disposed distal to the peripheral intravenous catheter, wherein the second catheter is snugly fit within the peripheral intravenous catheter such that in response to pushing the second catheter coupled to the guidewire through the peripheral intravenous catheter, the saline within the peripheral intravenous catheter exits a distal end of the peripheral intravenous catheter and is flushed into the vasculature.

10. The method of claim 9, further comprising coupling the connector to the peripheral intravenous catheter assembly, wherein the second catheter extends between about one and two inches beyond the distal end of the peripheral intravenous catheter when the connector is coupled to the peripheral intravenous catheter assembly.

11. The method of claim 10, further comprising when the connector is coupled to the peripheral intravenous catheter assembly, uncoupling a guidewire hub from a proximal end of the connector and removing the guidewire from within the second catheter such that the guidewire is no longer distal to the peripheral intravenous catheter, wherein a proximal end of the guidewire is secured within the guidewire hub.

12. The method of claim 11, further comprising using the peripheral intravenous catheter assembly coupled with the connector to infuse fluid or withdraw blood from a patient at least six hours after placement of the peripheral intravenous catheter assembly within vasculature of the patient.

* * * * *